(12) United States Patent
Bailly et al.

(10) Patent No.: US 7,041,290 B2
(45) Date of Patent: May 9, 2006

(54) MOLECULES AND METHODS FOR INHIBITING SHEDDING OF KIM-1

(75) Inventors: Veronique Bailly, Boxborough, MA (US); Joseph Bonventre, Wayland, MA (US)

(73) Assignees: Biogen Idec MA Inc., Cambridge, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 10/718,321

(22) Filed: Nov. 20, 2003

(65) Prior Publication Data

US 2005/0112117 A1 May 26, 2005

Related U.S. Application Data

(63) Continuation of application No. PCT/US02/17402, filed on May 31, 2002.

(60) Provisional application No. 60/295,907, filed on Jun. 4, 2001, provisional application No. 60/295,449, filed on Jun. 1, 2001.

(51) Int. Cl.
*A61K 39/395* (2006.01)

(52) U.S. Cl. .................. 424/133.1; 435/326; 530/387.1

(58) Field of Classification Search ............. 530/387.1; 435/326; 424/130.1, 133.1
See application file for complete search history.

(56) References Cited

U.S. PATENT DOCUMENTS

| | | | |
|---|---|---|---|
| 5,622,861 | A | 4/1997 | Kaplan et al. |
| 6,664,385 | B1 | 12/2003 | Sanicola-Nadel et al. |
| 2003/0124114 | A1 | 7/2003 | McIntire et al. |
| 2003/0215831 | A1 | 11/2003 | Sanicola-Nadel et al. |
| 2004/0005322 | A1 | 1/2004 | Kuchroo et al. |
| 2004/0180038 | A1 | 9/2004 | Hancock et al. |
| 2005/0095593 | A1 | 5/2005 | McIntire et al. |

FOREIGN PATENT DOCUMENTS

| | | |
|---|---|---|
| WO | WO 96/04376 | 2/1996 |
| WO | WO 97/44460 | 11/1997 |
| WO | WO 01/98481 | 12/2001 |
| WO | WO 03/025138 | 3/2003 |
| WO | WO 03/042661 | 5/2003 |
| WO | WO 03/080856 | 10/2003 |
| WO | WO 04/005544 | 1/2004 |
| WO | WO 04/084823 | 10/2004 |
| WO | WO 05/001092 | 1/2005 |

OTHER PUBLICATIONS

Rudikoff et al. 1982, Single amino acid substitution altering antigen-binding specificity, Proc. Nat. Acad. Sci., USA, 79:1979-1983.*

Thompson et al. Journal of Virology, vol. 72, No. 5,p. 3751-3761, 1998.*

Feigelstock et al., "The human homolog of HAVcr-1 codes for a hepatitis A virus cellular receptor," J. Virol. vol. 72, Aug. 1998, pp. 6621-6628.

Ichimura et al., "Kidney injury molecule-1 (KIM1), a putative epithelial cell adhesion molecule containing a novel immunoglobulin domain, is up-regulated in renal cells after injury," J. Biol. Chem. vol. 273, No. 7, Feb. 1998, pp. 4135-4142.

Owens et al., "The genetic engineering of monoclonal antibodies," J. Immunol. Methods. vol. 168, Feb. 10, 1994, pp. 149-165.

Bailly, V., et al., "Shedding of Kidney Injury Molecule-1, a Putative Adhesion Protein Involved in Renal Regeneration," Journal of Biological Chemistry, vol. 277, No. 42, Oct. 18, 2002, pp. 39739-39748.

Kaplan et al. (1996) "Identification of a Surface Glycoprotein on African Green Monkey Kidney Cells as a Receptor for Hepatitis A Virus," EMBO 15:4282-96.

Kuchroo, et al. (2003) "The *Tim* Gene Family: Emerging Roles in Immunity and Disease," Nat. Rev. Immunol. 3:454-62.

McIntire et al. (2001) "Identification of *Tapr* (An Airway Hyperreactivity Regulator Locus) and the Linked *Tim* Gene Family," Nat. Immunol. 2:1109-16.

Monney et al., (2002) "Th1-Specific Cell Surface Protein Tim-3 Regulates Macrophage Activation and Severity of an Autoimmune Disease," Nature 415:536-41.

* cited by examiner

*Primary Examiner*—Patrick J. Nolan
*Assistant Examiner*—Yunsoo Kim
(74) *Attorney, Agent, or Firm*—Fish & Richardson P.C.

(57) ABSTRACT

Disclosed are antibodies that inhibit proteolytic release of a soluble KIM-1 polypeptide from KIM-1 expressing cells. Also disclosed are methods of using the antibodies to inhibit shedding of the KIM-1 polypeptide.

40 Claims, 7 Drawing Sheets

FIGURE 1 A

```
                         ACA12
                         AKG7                                   ABE3
210                                                                                    290
MPLPRQNHEPVATSPSSPQPAETHPTTLQGAIRREPTSSPLYSYTTDGNDTVTESSDGLWNNNQTQLFLEHSLLTANTTKG
#43 MPLPRQNHEPVATSPSSP
       #44 PVATSPSSPQPAETHPTT
              #45 QPAETHPTTLQGAIRREP
                    #46 LQGAIRREPTSSPLYSYT
                            #47 TSSPLYSYTTDGNDTVTE
                                   #48 TDGNDTVTESSDGLWNNN
                                            #49 SSDGLWNNNQTQLFLEHS
                                                    #50 QTQLFLEHSLLTANTTKG
```

> human KIM-1(a)           334 aa
> human KIM-1(b) (HAVcr-1)  359 aa

MHPQVVILSLILHLADSVAGSVKVGGEAGPSVTLPCHYSGAVTSMCWNRGSCSLFTCQNG 60
IVWTNGTHVTYRKDTRYKLLGDLSRRDVSLTIENTAVSDSGVYCCRVEHRGWFNDMKITV 120
SLEIVPPKVTTTPIVTTVPTVTTVRTSTTVPTTTTVPTTTVPTTMSIPTTTTVPTTMTVS 180
TTTSVPTTTSIPTTTSVPVTTTVSTFVPPMPLPRQNHEPVATSPSSPQPAETHPTTLQGA 240
IRREPTSSPLYSYTTDG░░VTESSDGLWNN░░QLFLEHSLLTA░░KGIYAGVCISVL 300
VLLALLGVIIAKKYFFKKEVQQL { RPHKSCIHQRE 334
{ SVSFSSLQIKALQNAVEKEVQAEDNIYIENSLYATD 359

B.

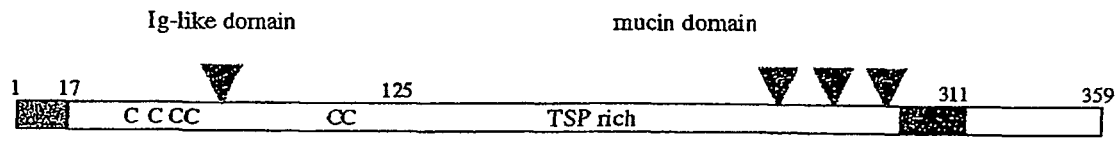

United States Patent

SEQUENCE LISTING

<160> NUMBER OF SEQ ID NOS: 8

<210> SEQ ID NO 1
<211> LENGTH: 18
<212> TYPE: PRT
<213> ORGANISM: Homo Sapiens

<400> SEQUENCE: 1

Ser Ser Asp Gly Leu Trp Asn Asn Asn Gln Thr Gln Leu Phe Leu Glu
1               5                   10                  15

His Ser

<210> SEQ ID NO 2
<211> LENGTH: 9
<212> TYPE: PRT
<213> ORGANISM: Homo Sapiens

<400> SEQUENCE: 2

Val Lys Val Gly Gly Glu Ala Gly Pro
1               5

<210> SEQ ID NO 3
<211> LENGTH: 9
<212> TYPE: PRT
<213> ORGANISM: Artificial Sequence
<220> FEATURE:
<223> OTHER INFORMATION: Consensus sequence

<400> SEQUENCE: 3

Leu Gln Gly Ala Ile Arg Arg Glu Pro
1               5

<210> SEQ ID NO 4
<211> LENGTH: 20
<212> TYPE: PRT
<213> ORGANISM: Homo Sapiens

<400> SEQUENCE: 4

Cys Lys Glu Val Gln Ala Glu Asp Asn Ile Tyr Ile Glu Asn Ser Leu
1               5                   10                  15

Tyr Ala Thr Asp
            20

<210> SEQ ID NO 5
<211> LENGTH: 15
<212> TYPE: PRT
<213> ORGANISM: Homo Sapiens
<220> FEATURE:
<221> NAME/KEY: VARIANT
<222> LOCATION: 11, 13, 15
<223> OTHER INFORMATION: Xaa = Any Amino Acid

<400> SEQUENCE: 5

Ser Val Lys Val Gly Gly Glu Ala Gly Pro Xaa Val Xaa Leu Xaa
1               5                   10                  15

<210> SEQ ID NO 6
<211> LENGTH: 81
<212> TYPE: PRT
<213> ORGANISM: Homo Sapiens

<400> SEQUENCE: 6

Met Pro Leu Pro Arg Gln Asn His Glu Pro Val Ala Thr Ser Pro Ser
1               5                   10                  15

Ser Pro Gln Pro Ala Glu Thr His Pro Thr Thr Leu Gln Gly Ala Ile
                20                  25                  30

Arg Arg Glu Pro Thr Ser Ser Pro Leu Tyr Ser Tyr Thr Thr Asp Gly
            35                  40                  45

Asn Asp Thr Val Thr Glu Ser Ser Asp Gly Leu Trp Asn Asn Asn Gln
        50                  55                  60

Thr Gln Leu Phe Leu Glu His Ser Leu Leu Thr Ala Asn Thr Thr Lys
65                  70                  75                  80

Gly

<210> SEQ ID NO 7
<211> LENGTH: 334
<212> TYPE: PRT
<213> ORGANISM: Homo Sapiens

<400> SEQUENCE: 7

Met His Pro Gln Val Val Ile Leu Ser Leu Ile Leu His Leu Ala Asp
1               5                   10                  15

Ser Val Ala Gly Ser Val Lys Val Gly Gly Glu Ala Gly Pro Ser Val
                20                  25                  30

```
Thr Leu Pro Cys His Tyr Ser Gly Ala Val Thr Ser Met Cys Trp Asn
            35                  40                  45
Arg Gly Ser Cys Ser Leu Phe Thr Cys Gln Asn Gly Ile Val Trp Thr
        50                  55                  60
Asn Gly Thr His Val Thr Tyr Arg Lys Asp Thr Arg Tyr Lys Leu Leu
 65                  70                  75                  80
Gly Asp Leu Ser Arg Asp Val Ser Leu Thr Ile Glu Asn Thr Ala
                85                  90                  95
Val Ser Asp Ser Gly Val Tyr Cys Cys Arg Val Glu His Arg Gly Trp
            100                 105                 110
Phe Asn Asp Met Lys Ile Thr Val Ser Leu Glu Ile Val Pro Pro Lys
        115                 120                 125
Val Thr Thr Thr Pro Ile Val Thr Thr Val Pro Thr Val Thr Thr Val
        130                 135                 140
Arg Thr Ser Thr Thr Val Pro Thr Thr Thr Val Pro Thr Thr Thr
145                 150                 155                 160
Val Pro Thr Thr Met Ser Ile Pro Thr Thr Thr Val Pro Thr Thr
                165                 170                 175
Met Thr Val Ser Thr Thr Ser Val Pro Thr Thr Ser Ile Pro
                180                 185                 190
Thr Thr Thr Ser Val Pro Val Thr Thr Val Ser Thr Phe Val Pro
                195                 200                 205
Pro Met Pro Leu Pro Arg Gln Asn His Glu Pro Val Ala Thr Ser Pro
        210                 215                 220
Ser Ser Pro Gln Pro Ala Glu Thr His Pro Thr Thr Leu Gln Gly Ala
225                 230                 235                 240
Ile Arg Arg Glu Pro Thr Ser Ser Pro Leu Tyr Ser Tyr Thr Thr Asp
                245                 250                 255
Gly Asn Asp Thr Val Thr Glu Ser Ser Asp Gly Leu Trp Asn Asn Asn
                260                 265                 270
Gln Thr Gln Leu Phe Leu Glu His Ser Leu Leu Thr Ala Asn Thr Thr
        275                 280                 285
Lys Gly Ile Tyr Ala Gly Val Cys Ile Ser Val Leu Val Leu Leu Ala
        290                 295                 300
Leu Leu Gly Val Ile Ile Ala Lys Lys Tyr Phe Phe Lys Lys Glu Val
305                 310                 315                 320
Gln Gln Leu Arg Pro His Lys Ser Cys Ile His Gln Arg Glu
                325                 330

<210> SEQ ID NO 8
<211> LENGTH: 359
<212> TYPE: PRT
<213> ORGANISM: Homo Sapiens

<400> SEQUENCE: 8

Met His Pro Gln Val Val Ile Leu Ser Leu Ile Leu His Leu Ala Asp
 1               5                  10                  15
Ser Val Ala Gly Ser Val Lys Val Gly Gly Glu Ala Gly Pro Ser Val
            20                  25                  30
Thr Leu Pro Cys His Tyr Ser Gly Ala Val Thr Ser Met Cys Trp Asn
            35                  40                  45
Arg Gly Ser Cys Ser Leu Phe Thr Cys Gln Asn Gly Ile Val Trp Thr
        50                  55                  60
Asn Gly Thr His Val Thr Tyr Arg Lys Asp Thr Arg Tyr Lys Leu Leu
```

-continued

```
            65                  70                  75                  80
Gly Asp Leu Ser Arg Arg Asp Val Ser Leu Thr Ile Glu Asn Thr Ala
                    85                  90                  95

Val Ser Asp Ser Gly Val Tyr Cys Cys Arg Val Glu His Arg Gly Trp
                100                 105                 110

Phe Asn Asp Met Lys Ile Thr Val Ser Leu Glu Ile Val Pro Pro Lys
                115                 120                 125

Val Thr Thr Thr Pro Ile Val Thr Thr Val Pro Thr Val Thr Thr Val
            130                 135                 140

Arg Thr Ser Thr Thr Val Pro Thr Thr Thr Val Pro Thr Thr Thr
145                 150                 155                 160

Val Pro Thr Thr Met Ser Ile Pro Thr Thr Thr Val Pro Thr Thr
                165                 170                 175

Met Thr Val Ser Thr Thr Ser Val Pro Thr Thr Thr Ser Ile Pro
                180                 185                 190

Thr Thr Thr Ser Val Pro Val Thr Thr Val Ser Thr Phe Val Pro
            195                 200                 205

Pro Met Pro Leu Pro Arg Gln Asn His Glu Pro Val Ala Thr Ser Pro
    210                 215                 220

Ser Ser Pro Gln Pro Ala Glu Thr His Pro Thr Thr Leu Gln Gly Ala
225                 230                 235                 240

Ile Arg Arg Glu Pro Thr Ser Ser Pro Leu Tyr Ser Tyr Thr Thr Asp
                245                 250                 255

Gly Asn Asp Thr Val Thr Glu Ser Ser Asp Gly Leu Trp Asn Asn Asn
            260                 265                 270

Gln Thr Gln Leu Phe Leu Glu His Ser Leu Leu Thr Ala Asn Thr Thr
            275                 280                 285

Lys Gly Ile Tyr Ala Gly Val Cys Ile Ser Val Leu Val Leu Leu Ala
    290                 295                 300

Leu Leu Gly Val Ile Ile Ala Lys Lys Tyr Phe Phe Lys Lys Glu Val
305                 310                 315                 320

Gln Gln Leu Ser Val Ser Phe Ser Ser Leu Gln Ile Lys Ala Leu Gln
                325                 330                 335

Asn Ala Val Glu Lys Glu Val Gln Ala Glu Asp Asn Ile Tyr Ile Glu
                340                 345                 350

Asn Ser Leu Tyr Ala Thr Asp
            355
```

US 7,041,290 B2

MOLECULES AND METHODS FOR INHIBITING SHEDDING OF KIM-1

This application is a continuation of International Patent Application No. PCT/US02/17402, filed May 31, 2002, which claims priority to U.S. Provisional Application Nos. 60/295,449, filed Jun. 1, 2001, expired, and 60/295,907, filed Jun. 4, 2001, expired.

FIELD OF THE INVENTION

The invention relates to antibodies that bind to polypeptides expressed in injured or diseased kidney cells, as well as to methods for production and the use of such antibodies.

BACKGROUND OF THE INVENTION

The kidney injury-molecule-1 ("KIM-1") gene was identified as a gene whose expression is upregulated in post-ischemic rat kidney cells as compared to the expression of the gene in non-injured rat kidney cells. The KIM-1 gene encodes a type I cell membrane glycoprotein. Two forms of the gene have been described in humans. One form is named KIM-1(a) and is 334 amino acids in length. The second form is named KIM-1(b) and is 359 amino acids in length. The two human homologues are identical throughout their 323 amino terminal amino acid sequences but differ in sequence in their carboxy terminal amino acids. The KIM-1 gene is expressed in dedifferentiated proximal tubular epithelial cells in damaged regions. High level expression is observed in the S3 segment of the proximal tubule in the outer stripe of the outer medulla. This region is highly susceptible to damage as a result of ischemia or toxins.

The amino terminal region of the KIM-1 protein includes the extracellular portion of the KIM-1 protein. This region includes a six-cysteine immunoglobulin-like domain and a T/SP rich domain characteristic of mucin-like O-glycosylated proteins. Immunoglobulin-like domains have been widely implicated in mediating protein-protein interactions, particularly at the cell surface where they are responsible for cell-cell and cell-extracellular matrix interactions.

SUMMARY OF THE INVENTION

The invention is based in part on the discovery that monoclonal antibodies raised against the human KIM-1 extracellular domain can inhibit proteolytic release (shedding) of a soluble KIM-1 polypeptide from the membrane-associated form of the KIM-1 protein.

In general, the invention features an antibody, antibody derivative, or antigen-binding polypeptide that inhibits proteolytic release of a soluble KIM-1 polypeptide from KIM-1-expressing cells. The antibody can be a monoclonal antibody or a polyclonal antibody. The antibody can be a humanized monoclonal antibody or a fully human monoclonal antibody. The antibody can include, e.g., an IgG polypeptide.

The antibody binds to the extracellular domain of a full length KIM-1 polypeptide. In some embodiments the antibody binds to an epitope located within the amino acid sequence SSDGLWNNNQTQLFLEHS (SEQ ID NO:1) in the extracellular domain of a KIM-1 polypeptide.

Also provided by the invention is a conjugate that includes a proteolysis-inhibiting KIM-1 antibody, antibody derivative or antigen binding polypeptide linked to a detectable label. The detectable label can be, e.g., a radiolabel or a fluorescent label.

The invention also includes a conjugate or fusion polypeptide that includes a KIM-1 proteolysis-inhibiting antibody, antibody derivative, or antigen-binding polypeptide and a toxin moiety.

Also within the invention is an antibody that has the same epitope specificity as the antibody produced by the hybridoma deposited in the ATCC under Accession No. PTA-3350.

The invention additionally provides an antibody that crossblocks binding of the antibody produced by the hybridoma deposited in the ATCC under Accession No. PTA-3350. In some embodiments, the antibody is produced by the hybridoma deposited with ATCC as Accession No. PTA-3350. Also featured by the invention is a nucleic acid encoding the monoclonal antibody produced by the hybridoma.

The invention also features the hybridoma deposited with ATCC under Accession No. PTA-3350.

The invention features a composition that includes the herein described KIM-1 proteolysis-inhibiting antibody, antibody derivative, or antigen-binding polypeptide and a pharmaceutically acceptable carrier.

The invention also includes a method of inhibiting release of a soluble form of a KIM-1 polypeptide from a cell. The method includes contacting a cell expressing a KIM-1 cell surface polypeptide with an effective amount of a KIM-1 proteolysis-inhibiting antibody, antibody derivative, or antigen-binding polypeptide. The cell can be, e.g., a renal cell. In some embodiments, the renal cell is a renal cancer cell.

The cell can be provided in vitro or in vivo. Preferably, the effective amount of antibody is between about 0.1 and 100 mg/kg, more preferably between about 0.5 and about 50 mg/kg, and still more preferably between about 1 and about 20 mg/kg. When the cell is provided in vivo, the effective amount of antibody can be administered by intravenous infusion into a subject during an infusion period of 1–6 hours. In some embodiments, the soluble form of the KIM-1 polypeptide includes the polypeptide sequence VKVGGEAGP (SEQ ID NO:2). Data from Example 3 revealed that a soluble form of KIM-1 which was released into the extracellular milieu by proteolytic cleavage at a site proximal to the transmembrane domain included the amino acid sequence given by SEQ ID NO:2.

Also provided by the invention is a method of inhibiting proteolytic shedding of a KIM-1 fragment by contacting a cell expressing a KIM-1 polypeptide comprising the fragment with an effective amount of a KIM-1 proteolysis-inhibiting antibody, antibody derivative, or antigen-binding polypeptide.

The invention also includes a method of treating or preventing renal disease or injury. The method includes administering to a mammal, e.g., a human, in need thereof a KIM-1 proteolysis-inhibiting antibody, antibody derivative, or antigen-binding polypeptide. An example of a renal disease that can be treated is renal cancer, e.g., renal carcinoma.

As used herein, the term "antibody" refers to an immunoglobulin molecule and immunologically-active portions of the immunoglobulin molecule, i.e., a molecule that contains an antigen binding site that specifically-binds (immunoreacts with) an antigen. Such antibodies include, but are not limited to, polyclonal, monoclonal, chimeric, single chain, Fab and F(ab')$_2$ fragments, and an Fab expression library.

As used herein, the term "derivative" refers to a molecule that contains either additional chemical moieties that are not normally a part of the molecule or contains less moieties than are normally a part of the molecule. The addition or subtraction of moieties may improve the molecule's solubility, absorption, or biological half-life or may decrease the toxicity of the molecule.

As used herein, the term "antigen-binding polypeptide" refers to an antibody fragment, variant, analog, or chemical derivative that retains the antigen-binding properties of the antibody.

As used herein, the term "monoclonal antibody" (MAb) refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it.

As used herein, the term "KIM-1 proteolysis-inhibiting antibody" refers to an antibody that inhibits proteolytic release of a soluble KIM-1 polypeptide.

As used herein, the term "crossblocking antibody" refers to an antibody that lowers the amount of binding of anti-KIM-1 antibody to an epitope on a KIM-1 polypeptide relative to the amount of binding of the anti-KIM-1 antibody to the epitope in the absence of the antibody.

As used herein, the term "conjugate" refers to an antibody covalently linked to a second moiety. The second moiety can be, e.g., a label.

As used herein, the term "label" refers to a molecular moiety capable of detection. A label can be, e.g., a radioactive isotope, enzyme, luminescent agent, or a dye.

As used herein, the term "fusion polypeptide" refers to an anti-KIM-1 antibody molecule operatively linked to a non-anti-KIM-1 antibody molecule.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE DRAWINGS

FIG. 1A is a schematic illustration showing the polypeptide sequence of the human KIM-1 mucin domain (SEQ ID NO: 6) and corresponding 18-mer overlapping synthetic peptides used to map the binding epitopes of monoclonal antibodies ACA12, AKG7 and ABE3.

FIGS. 2A–3C are representations of Western blot analysis of cell reacted with AGE3 (FIG. 2A), cell extracts reacted with rabbit pilyclonal anibodies against the human KIM-1 (b) C-terminus (FIG. 2B), and conditioned media reacted with monoclonal antigody AKG7(FIG. 2C).

FIGS. 3A–3C are representations of Western blot analyses of COS-7 cell extracts or conditioned media reacted with AKG7 (FIG. 3A), ABE3 (FIG. 3B), or rabbit polyclonal antibodies raised against the human KIM-1(b) C-terminus (FIG. 3C).

FIG. 6A is a sequence of human KIM-1(a) (SEQ ID NO: 7) and human HAVcr-1 or KIM-1(b) (SEQ ID NO: 8). A single sequence is represented up to residue 323 corresponding to the sequence common to the two polypeptides. Underlined are the putative signal sequence and transmembrane domain. Shaded are the four putative N-glycosylation motifs. Italicized is the sequence of the synthetic peptide used to raise antibodies against the C-terminus of KIM-1(b).

FIG. 6B is a schematic representation of the KIM-1(b) protein. Grey boxes represent the signal sequence and the transmembrane domain. Cysteine residue in the Ig-like domain are marked (C). The four triangles represent putative N-glycans. The TSP-rich region is thickened to schematize the mucin-like domain.

DETAILED DESCRIPTION OF THE INVENTION

Figure 1B:
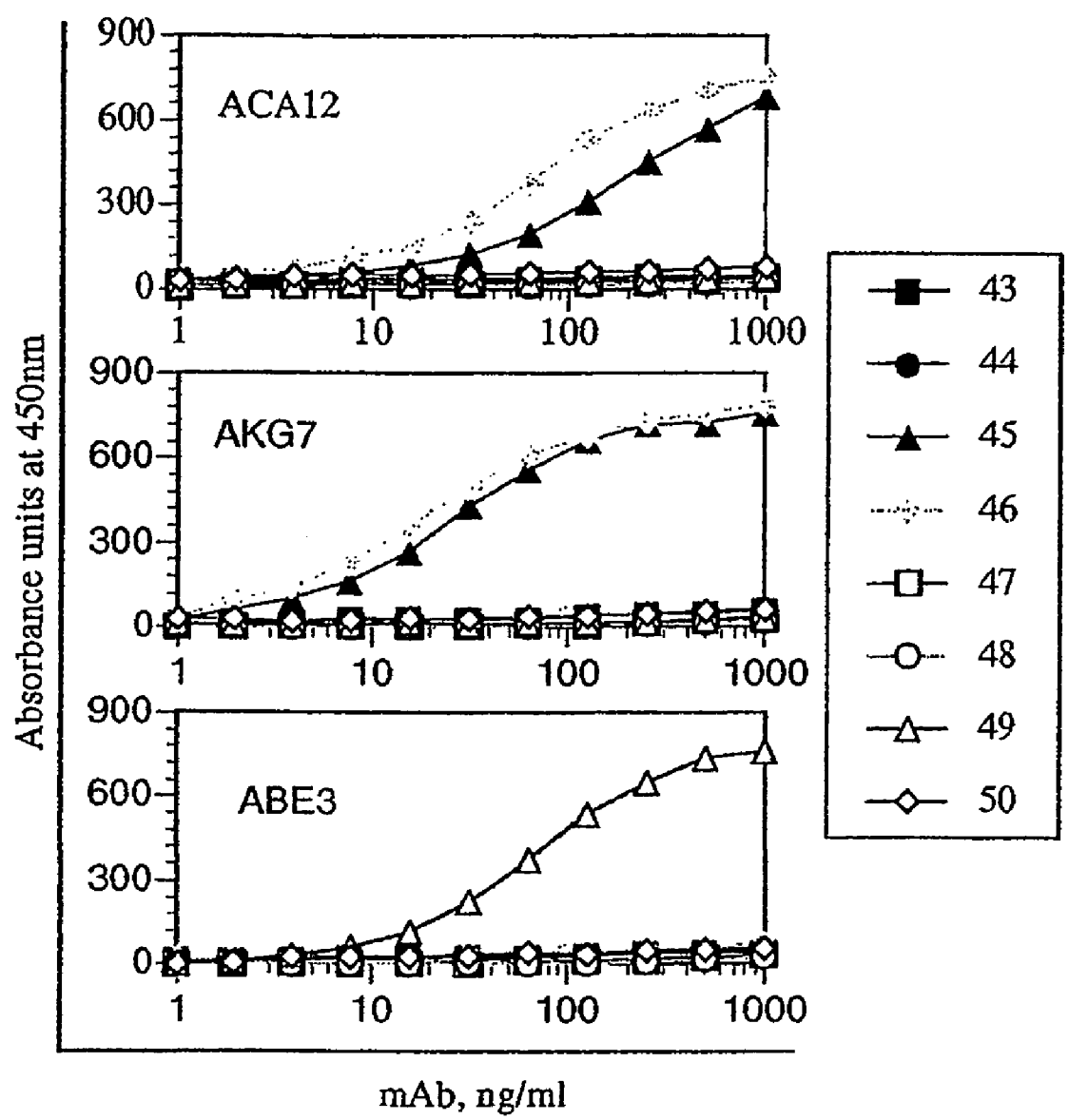
FIG. 1B is a set of graphs showing binding of monoclonal antibodies ABE3, AKG7 and ACA12 to peptides 43 to 50 at various concentrations of antibody (peptide 43 corresponds to amino acids 210–227 of SEQ ID NO:7; peptide 44 corresponds to amino acids 219–236 of SEQ ID NO:7; peptide 45 corresponds to amino acids 228–245 of SEQ ID NO:7; peptide 46 corresponds to amino acids 237–254 of SEQ ID NO:7; peptide 47 corresponds to amino acids 246–263 of SEQ ID NO:7; peptide 48 corresponds to amino acids 255–272 of SEQ ID NO:7; peptide 49 corresponds to amino acids 264–281 of SEQ ID NO:7; and peptide 50 corresponds to amino acids 273–290 of SEQ ID NO:7).

The present invention features antibodies that bind specifically to a KIM-1 polypeptide and inhibit proteolytic release of a soluble form of KIM-1 from KIM-1 expressing cells.

KIM-1 is one of a number of membrane proteins that also exist in a soluble (truncated) form. Although these soluble forms can result from alternative splicing, they more often derive from proteolysis of the membrane form. The cleavage occurs close to the transmembrane domain, resulting in the release of physiologically active protein.

The antibodies described herein can be used to detect a cell expressing a KIM-1 polypeptide, e.g., a kidney cell. Because KIM-1 polypeptides are expressed at high levels in post-ischemic or diseased kidney cells, the antibodies disclosed herein are useful for detecting injured or diseased kidney cells in a subject. The antibodies can also be used to inhibit proteolytic cleavage of a KIM-1 polypeptide, and thereby inhibit functions or processes mediated by soluble forms of a KIM-1 polypeptide. The antibodies can also be administered to a subject to treat or prevent renal disease or injury in a subject.

Anti-KIM-1 Antibodies that Inhibit Proteolytic Release of a Soluble KIM-1 Polypeptide To prepare proteolysis-inhibiting KIM-1 antibodies, immunogens are used that include the extracellular domain of a KIM-1 polypeptide. The extracellular domain extends from amino acids 1 to 290 of the human KIM-1 polypeptide. The amino acid sequences of human and rat KIM-1 polypeptides, and the nucleic acids encoding the polypeptides, are provided in WO97/44460, published Nov. 27, 1997, and in Ichimura et al. (1998) J. Biol. Chem. 273:4135–42.

Suitable antibodies include, e.g., polyclonal, monoclonal, chimeric, single chain, $F_{ab}$, $F_{ab'}$, $F_{sc}$, $F_v$, and $F_{(ab')2}$ fragments, and an $F_{ab}$ expression library. In general, an antibody molecule obtained from humans can be classified in one of the immunoglobulin classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

The extracellular domain of the KIM-1 polypeptide, or a portion or fragment thereof, can serve as an antigen, and additionally can be used as an immunogen to generate antibodies that immunospecifically bind the antigen, using standard techniques for polyclonal and monoclonal antibody preparation. Preferably, the antigenic peptide comprises at least 10 amino acid residues, or at least 15 amino acid residues, or at least 20 amino acid residues, or at least 30 amino acid residues. A preferred anti-KIM-1 antibody binds to an epitope within, overlapping, or in close proximity to the amino acid sequence SSDGLWNNNQTQLFLEHS (SEQ ID NO: 1) in KIM-1. The results obtained in Example 2 suggested that a binding epitope of the anti-KIM-1 antibody ABE3 to the KIM-1 polypeptide is around the portion of the amino acid sequence of KIM-1 polypeptide given by SEQ ID NO: 1.

Various procedures known in the art may be used for the production of polyclonal or monoclonal antibodies that inhibit proteolytic release of a soluble KIM-1 polypeptide from KIM-1-expressing cells. See, for example, ANTIBODIES: A LABORATORY MANUAL, Harlow and Lane (1988) Cold Spring Harbor Laboratory Press, Cold Spring Harbor, N.Y. Some of these antibodies are discussed below. Antibodies generated against the KIM-1 polypeptide can be characterized to identify their binding epitopes using methods known in the art, including those described in Example 2, below. Antibodies can be screened to identify those that inhibit proteolytic release of soluble forms of KIM-1 using methods such as those described in Example 4, below.

Some proteolysis-inhibiting antibodies have the same epitope specificity as the antibody produced by the hybridoma producing monoclonal antibody ABE3. Also contemplated are antibodies that crossblock binding of the monoclonal antibody ABE3 to an epitope present on a KIM-1 polypeptide. Crossblocking antibodies can be identified by comparing the binding of the monoclonal antibody ABE3 to a KIM-1 polypeptide in the presence and absence of a test antibody. Decreased binding of the ABE3 monoclonal antibody in the presence of the test antibody as compared to binding of the ABE3 monoclonal antibody in the absence of the test antibody indicates the test antibody is a crossblocking antibody.

Polyclonal Antibodies

For the production of polyclonal antibodies, any suitable animal (e.g., rabbit, goat, mouse or other mammal) may be immunized by one or more injections of a polypeptide that includes the KIM-1 ectodomain. The polypeptide can be, for example, the naturally occurring KIM-1, a chemically synthesized polypeptide representing the ectodomain, or a recombinantly expressed fusion protein. The fusion moiety or a chemically conjugated moiety can be a second protein known to be immunogenic in the mammal being immunized. Examples of such immunogenic proteins include but are not limited to keyhole limpet hemocyanin, serum albumin, bovine thyroglobulin, and soybean trypsin inhibitor.

The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), adjuvants usable in humans such as Bacille Calmette-Guerin and *Corynebacterium parvum*, or similar immunostimulatory agents. Additional examples of adjuvants which can be employed include MPL-TDM adjuvant (monophosphoryl Lipid A, synthetic trehalose dicorynomycolate).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by Wilkinson. Wilkinson (2000) The Scientist 14: 25–28.

Monoclonal Antibodies and Hybridomas

Monoclonal antibodies can be prepared using hybridoma methods, such as those described by Kohler and Milstein (1975) Nature 256:495. In a hybridoma method, a mouse, hamster, or other appropriate host animal, is typically immunized with an immunizing agent to elicit lymphocytes that produce or are capable of producing antibodies that will specifically bind to the immunizing agent.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Goding, MONOCLONAL ANTIBODIES: PRINCIPLES AND PRACTICE, Academic Press, (1986) pp. 59–103. Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor (1984) J. Immunol. 133:3001; Brodeur et al., MONOCLONAL ANTIBODY PRODUCTION TECHNIQUES AND APPLICATIONS, Marcel Dekker, Inc., N.Y., (1987) pp. 51–63).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard (1980) Anal. Biochem. 107:220. Preferably, antibodies having a high degree of specificity and a high binding affinity for the target antigen are isolated.

After the desired hybridoma cells are identified, the clones can be subcloned by limiting dilution procedures and grown by standard methods. Suitable culture media for this purpose include, for example, Dulbecco's Modified Eagle's Medium and RPMI-1640 medium. Alternatively, the hybridoma cells can be grown in vivo as ascites in a mammal.

A hybridoma that produces monoclonal antibody subclone ABE3.16 was deposited with the American Type Culture Collection at 10801 University Boulevard, Manassas, VA 20110-2209 (U.S.A.) on May 2, 2001, and has been assigned Accession Number PTA-3350. ABE3.16 is a subclone of ABE3.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of interest can be readily isolated and sequenced using conventional procedures (e.g., by using oligonucleotide probes that bind specifically to genes encoding the heavy and light chains of murine antibodies). The hybridoma cells of the invention serve as a preferred source of such DNA. Cloning of immunoglobulin variable region genes using the polymerase chain reaction (PCR) is an established technique. See, e.g., Kettleborough et al., 1993, Eur. J. Immunol. 23:206–211. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells.

The DNA also can be modified, for example, by substituting the coding sequence for human heavy and light chain constant domains in place of the homologous murine sequences (U.S. Pat. No. 4,816,567; Morrison (1994) Nature 368:812–13) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Humanized Antibodies

The antibodies directed against the protein antigens of the invention can further comprise humanized antibodies or human antibodies. These antibodies are suitable for administration to humans without causing a strong immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al. (1986) Nature 321:522–525; Riechmann et al. (1988) Nature 332:323–327; Verhoeyen et al. (1988) Science 239:1534–1536), by substituting rodent CDRs or CDR sequences for the corresponding sequences of a human antibody. (See also U.S. Pat. No. 5,225,539.) In some instances, Fv framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta (1992) Curr. Op. Struct. Biol. 2:593–596).

Human Antibodies

Fully human antibodies relate to antibody molecules in which essentially the entire sequences of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor et al. (1983) Immunol. Today 4: 72) and the EBV hybridoma technique to produce human monoclonal antibodies (see Cole et al. 1985 In: MONOCLONAL ANTIBODIES AND CANCER THERAPY, Alan R. Liss, Inc., pp. 77–96). Human monoclonal antibodies may be produced by using human hybridomas (see Cote, et al. (1983) Proc. Natl. Acad. Sci. USA 80: 2026–2030) or by transforming human B-cells with Epstein Barr Virus in vitro (see Cole, et al. (1985) In: MONOCLONAL ANTIBODIES AND CANCER THERAPY, Alan R. Liss, Inc., pp. 77–96).

In addition, human antibodies can also be produced using additional techniques, including phage display libraries. Hoogenboom and Winter (1991) J. Mol. Biol., 227:381; Marks et al. (1991) J. Mol. Biol., 222:581. Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (Bio/Technology 10:779–783 (1992)); Lonberg et al. (Nature 368:856–859 (1994)); Morrison (Nature 368: 812–813 (1994)); Fishwild et al.,(Nature Biotechnology 14: 845–51 (1996)); Neuberger (Nature Biotechnology 14: 826 (1996)); and Lonberg and Huszar (Intern. Rev. Immunol. 13:65–93 (1995)).

Human antibodies may additionally be produced using transgenic nonhuman animals which are modified so as to produce fully human antibodies rather than the animal's endogenous antibodies in response to challenge by an antigen. See, e.g., PCT publication WO94/02602. The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method useful for producing an antibody of the invention, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain. Additional useful procedures, i.e., a method for identifying a clinically relevant epitope on an immunogen, and a correlative method for selecting an antibody that binds immunospecifically to the relevant epitope with high affinity, are disclosed in PCT publication WO 99/53049.

$F_{ab}$ Fragments and Single Chain Antibodies

Techniques can be adapted for the production of single-chain antibodies specific to an antigenic protein (see e.g., U.S. Pat. No. 4,946,778). In addition, methods can be adapted for the construction of Fab expression libraries (see e.g., Huse et al. (1989) Science 246:1275–1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab'}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Immunoconjugates

The antibodies described herein can be conjugated to an agent such as a chemotherapeutic agent, imaging agent, toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$In, $^{90}$Y, and $^{186}$Re.

Conjugates of the antibody and cytotoxic agent can be made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., (1987) Science 238:1098. Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

The antibodies described herein can also be labeled with an imaging reagent that produces a detectable signal. Imaging reagents and procedures for labeling antibodies with such reagents are well known (see, e.g., Wensel and Meares, Radio Immunoimaging and Radioimmunotherapy, Elsevier, N.Y., (1983); Colcher et al., Meth. Enzymol. (1986) 121: 802–16. The labeled antibody can be detected using art-recognized techniques, including, e.g., radionuclear scanning (see, e.g., Bradwell et al., in Monoclonal Antibodies for Cancer Detection and Therapy, Baldwin et al. (eds.) pp. 65–85, Academic Press (1985)).

Pharmaceutical Compositions

The antibodies described herein can be administered to a mammalian subject, e.g., a human, to image kidney cells or to treat kidney cell-associated disorders. The antibodies can be administered alone, or in a mixture. For example, the antibodies can be administered in the presence of a pharmaceutically acceptable excipient or carrier, such as physiological saline. The excipient or carrier is selected on the basis of the mode and route of administration. Suitable pharmaceutical carriers are described in Remington's Pharmaceutical Sciences (E. W. Martin), and in the USP/NF (United States Pharmacopeia and the National Formulary). A pharmaceutical composition is formulated to be compatible with its intended route of administration. Examples of routes of administration include, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, polypropylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

The pharmaceutical compositions of the invention may include a "therapeutically effective amount" or a "prophylactically effective amount" of an antibody, antibody derivative, or antigen-binding polypeptide of the invention. As used herein, "therapeutically effective amount" means an amount effective, at dosages, and for periods of time necessary, to achieve the desired therapeutic result. A therapeutically effective amount of the antibody, antibody derivative, or antigen-binding polypeptide can vary according to factors such as the disease state, age, sex, and weight of the individual, and the ability of the antibody, antibody derivative, or antigen-binding polypeptide to elicit a desired response in an individual. When a therapeutically effective amount is administered, any toxic or detrimental effects of the antibody, antibody derivative, or antigen-binding polypeptide are outweighed by the therapeutically beneficial effects. As used herein, "prophylactically effective amount" means an amount effective, at dosages, and for periods of time necessary, to achieve the desired prophylactic result. Because a prophylactic dose is administered in subjects prior to onset of disease, the prophylactically effective amount typically is less than the therapeutically effective amount.

Dosage regimens can be adjusted to provide the optimum desired response, e.g., a therapeutic or prophylactic response. For example, in some embodiments of the invention a single bolus is administered. In other embodiments, several divided doses are administered over time. The dose can be reduced or increased proportionately, as indicated by the exigencies of the situation. It is advantageous to formulate parenteral compositions in dosage unit form for ease of administration and uniformity of dosage. As used herein, "dosage unit form" means physically discrete units suitable as unitary dosages for the mammalian subjects to be treated, with each containing a predetermined quantity of active ingredient calculated to produce the desired therapeutic effect in association with the required pharmaceutical carrier.

An exemplary, non-limiting range for a therapeutically or prophylactically effective amount of an antibody or antibody portion of the invention is 0.1–100 mg/kg, preferably 0.5–50 mg/kg, more preferably 1–20 mg/kg, and even more preferably 1–10 mg/kg. Dosage values may vary with the type and severity of the condition being treated. For any particular subject, specific dosage regimens should be adjusted over time according to the individual need and the professional judgment of the person administering or supervising the administration of the compositions. It is to be understood that dosage ranges set forth herein are exemplary only and are not intended to limit the scope of the claimed invention.

Parenteral injectable administration is generally used for subcutaneous, intramuscular or intravenous injections and infusions. Additionally, one approach for parenteral administration employs the implantation of a slow-release or sustained-released systems, which assures that a constant level of dosage is maintained, according to U.S. Pat. No. 3,710,795, incorporated herein by reference.

In general, a suitable subject is any mammal to which a KIM-1 antibody may be administered. Subjects specifically intended for treatment include humans, nonhuman primates, sheep, horses, cattle, goats, pigs, dogs, cats, rabbits, guinea pigs, hamsters, gerbils, rats and mice.

Renal conditions that may be beneficially treated include those in which inhibition of release of soluble KIM-1 from a cell expressing a KIM-1 cell surface protein can ameliorate the condition. Examples of such conditions are renal cancer or renal injury, including renal cancers such as renal carcinomas. Other conditions include, e.g., renal failure, chronic renal failure, acute nephritis, nephritic syndrome, renal tubule defects, kidney transplants, toxic injury, hypoxic injury, and trauma. Renal tubule defects include those of either hereditary or acquired nature, such as polycystic renal disease, medullary cystic disease, and medullary sponge kidney.

Deposits

A hybridoma which produces the monoclonal antibody ABE3.16 has been deposited with the American Type Culture Collection (ATCC) under the terms of the Budapest Treaty on the International Recognition of the Deposit of Microorganisms for the Purpose of Patent Procedure on May 2, 2001, and bears the accession number ATCC PTA-3350. Applicants acknowledge their duty to replace the deposit should the depository be unable to furnish a sample when requested due to the condition of the deposit before the end of the term of a patent issued hereon. Applicants also acknowledge their responsibility to notify the ATCC of the issuance of such a patent, at which time the deposit will be made available to the public. Prior to that time, the deposit will be made available to the Commissioner of Patents under the terms of 37C.F.R. § 1.14 and 35 U.S.C. § 112.

The invention is further illustrated by the following experimental examples. The examples are provided for illustration only, and are not to be construed as limiting the scope or content of the invention.

EXAMPLE 1

Generation of Anti-KIM-1 Monoclonal Antibodies

Monoclonal antibodies were generated against the extracellular domain of a human KIM-1 polypeptide. A construct (KIM-1-Ig) was constructed in which the extracellular domain of human KIM-1 (residues 1–290) was attached to the Fc portion of human IgG1 (hinge CH2+CH3 domains) and cloned into a mammalian expression plasmid pEAG347. A human KIM-1(b) full-length cDNA was obtained by RT-PCR using mRNA from the human carcinoma cell line 769-P and primers based on the published DNA sequence (Feigelstock et al. (1998) J. Virol. 72:6621–28).

The sequence of the cDNA obtained was identical to that of the cDNA obtained from human kidney and liver. The pEAG347 expression plasmid contains a tandem promoter (SV40 Early/Adenovirus Major late) for constitutive expression and the DHFR gene for methotrexate selection of stably expressing cell lines. Transfected CHO cell lines expressing the fusion proteins were selected, adapted in suspension, and grown in fermentors.

Four mice were immunized with human KIM-1-Ig. The increase of the antibody titer against KIM-1 was monitored by performing enzyme-linked immunoabsorbance assays (ELISA). The ELISAs were performed in 96-well plates (MaxiSorb, Nunc). Plates were coated by incubation overnight at 4° C. with 100 µl of antigen or trapping antibody in 50 mM sodium carbonate, pH 9.6. Potential remaining adsorption sites were then blocked with BSA by incubation for one hour at room temperature with 400 µl PBS containing 1% BSA. Plates were washed four times with PBST after each reaction step. Horseradish peroxidase (HRP) conjugates were used as secondary detection reagents, and the color reaction was performed with tetramethylbenzidine.

The mouse showing the highest serological titer against KIM-1 was identified and boosted with KIM-1-Ig. The mouse was then sacrificed, and its spleen cells were fused with FL653 myeloma cells at a 1:6 ratio of spleen cell per myeloma cell. The cell fusions were plated in 96 well tissue culture plates in selection media at a density of $10^5$ cells per well, a density of $3.3 \times 10^4$ cells per well, or a density of $1.1 \times 10^4$ cells per well. Wells positive for growth were screened by ELISA for expression of antibody against human KIM-1, and subcloned. At the end of the selection, the ten clones showing the strongest binding were retained and characterized by ELISA and western blot analysis. The results are shown below in Table 1.

fusion protein lacking the mucin domain (hKIM-1(mucin-min)-Ig). These results demonstrated that the binding epitopes for these antibodies are at least partly in the mucin domain. In addition, these four antibodies were the only antibodies observed to react with reduced denatured hKIM-1-Ig on a western blot. This observation indicated that the epitopes for these antibodies corresponded to a single stretch of amino acid residues in the protein primary structure.

Binding epitopes were identified by measuring binding of the antibodies to eight overlapping synthetic 18-mer peptides starting at KIM-1 residue 210, which lies within the mucin domain, and ending at residue 290, the last residue of the extracellular domain. The peptides used in the binding studies are presented in FIG. 1A relative to the KIM-1 polypeptide sequence. The results of the binding studies are shown in FIG. 1B for monoclonal antibodies ACA12, AKG7, and ABE3. Both AKG7 and ACA12 bound to peptides 45 and 46, although they differed in their respective binding affinities. From these results, it was concluded that both antibodies bound to a sequence including LQGAIR-REP (SEQ ID NO:3), which is a 9-residue sequence common to peptide 45 and 46 (FIG. 1A). This peptide sequence lacked putative sites for either N-linked or O-linked glycosylation, which suggested that ACA12 and AKG7 recognized both glycosylated and non-glycosylated forms of the KIM-1 polypeptide.

Monoclonal antibody ABE3 bound to peptide #49 but did not show substantial binding to either peptide #48 or #50. These observations suggested that the binding epitope of ABE3 is around DGLWNNNQTQL (amino acids 3–13 of SEQ ID NO:1). This sequence includes a potential glyco-

TABLE 1

| | CLONE | | | | | | | | | |
|---|---|---|---|---|---|---|---|---|---|---|
| Isotype | AUF1 G1k | ASG1 G2b | ACA12 G1k | ABE3 G1k | ATE11 G1k | AMC12 G1k | AKG7 G1k | BIE6 G1k | AWE2 G1k | ARD5 G1k |
| ELISA on hKIM-1-Ig | + | + | + | + | + | + | + | + | + | + |
| ELISA on hKIM-1(mucin-minus)-Ig | + | + | − | − | − | + | − | + | + | + |
| Western blot KIM-1-Ig reduced | − | − | + | + | + | − | + | − | − | − |
| Western blot KIM-1-Ig nonreduced | + | + | + | + | + | + | + | + | + | + |

Four hybridoma clones (ABE3, ACA12, AKG7, and ARD5) were grown in the peritoneal cavity of mice. The ascitic fluid was collected, and each antibody was purified by chromatography using protein A Sepharose. Biotinylated AKG7 was prepared by directed binding of amino-reactive sulfo-NHS-LC-biotin (Pierce).

EXAMPLE 2

Identification of Binding Epitopes of Anti-KIM-1 Monoclonal Antibodies

The monoclonal antibodies produced by hybridomas ABE3, ACA12, AKG7, and ATE11 failed to bind to a KIM-1 sylation site at the last asparagine residue. However, since ABE3 bound to synthetic peptides as well as to various glycosylated forms of KIM-1, it was concluded that binding of ABE3 is primarily to a peptide moiety.

EXAMPLE 3

Identification of a Shed form of a KIM-1 Polypeptide

This example demonstrated that soluble forms of KIM-1 polypeptides are released from KIM-1 expressing cells.

Three kidney and one liver human cell lines were analyzed by western blot for expression of KIM-1. The cell lines used were 293 (embryonic kidney cells transformed with adenovirus: CRL-1573), HK2 (human kidney proximal tubular cells transduced with HPV-16; CRL-2190), 769-P (human renal cell adenocarcinoma; CRL-1933) and HepG2 (hepatocellular carcinoma; HB-8065). Protein from cell extracts or conditioned media were analyzed by Western blot and probed with ABE3 monoclonal antibody, AKG7 monoclonal antibody, or a rabbit polyclonal antibody raised against the carboxyterminal portion of the KIM-1(b) protein. The rabbit polyclonal antibody was raised against a synthetic peptide (CKEVQAEDNIYIENSLYATD (SEQ ID NO:4); Research Genetics) corresponding to the last 19 amino acid residues at the C-terminus of the human KIM-1(b) protein, plus an additional cysteine residue for the conjugation. The peptide was conjugated to maleimide-activated KLH (Pierce) and the conjugate was used to immunize a rabbit. Antisera were collected after several immunizations.

The conditioned medium and the cells were harvested at approximately 90% cell confluency. The cells were rinsed with PBS and scraped with a rubber policeman in ice-cold PBS containing 5 mM EDTA and a cocktail of protease inhibitors (Boehringer Mannheim, Mini tablet). The cells were pelleted and lysed by resuspension in 50 mM HEPES, 150 mM NaCl, pH 7.5, 1% NP-40 with protease inhibitors (20 µl of lysis solution per mg of cell pellet). After 5 minutes on ice, the insoluble material was collected by centrifugation for 5 minutes at 16000 g and the supernatant was mixed with 2× reducing loading buffer. An aliquot of each conditioned medium was also mixed with an equal volume of 2× reducing loading buffer.

For SDS-PAGE and western blot analysis, protein samples were mixed with reducing loading buffer and heated for 5 minutes at 95° C. Reduced and denatured proteins were then separated by SDS-PAGE on 4–20% polyacrylamide gels. The proteins were transferred onto a nitrocellulose sheet. The blot was blocked with a solution of 5% non fat dry milk (Carnation) in PBST and probed in the same solution with the murine monoclonal antibodies AKG7, ABE3 or ACA12 (at 1 µg/ml) or with the rabbit polyclonal antiserum raised against the C-terminal peptide of KIM-1(b) (diluted 1000 fold), followed by either goat anti-murine or goat anti-rabbit antibodies conjugated to horse-radish peroxidase. Washes between the steps were performed with PBST. Reactive bands were revealed by chemiluminescence.

Figure 2:
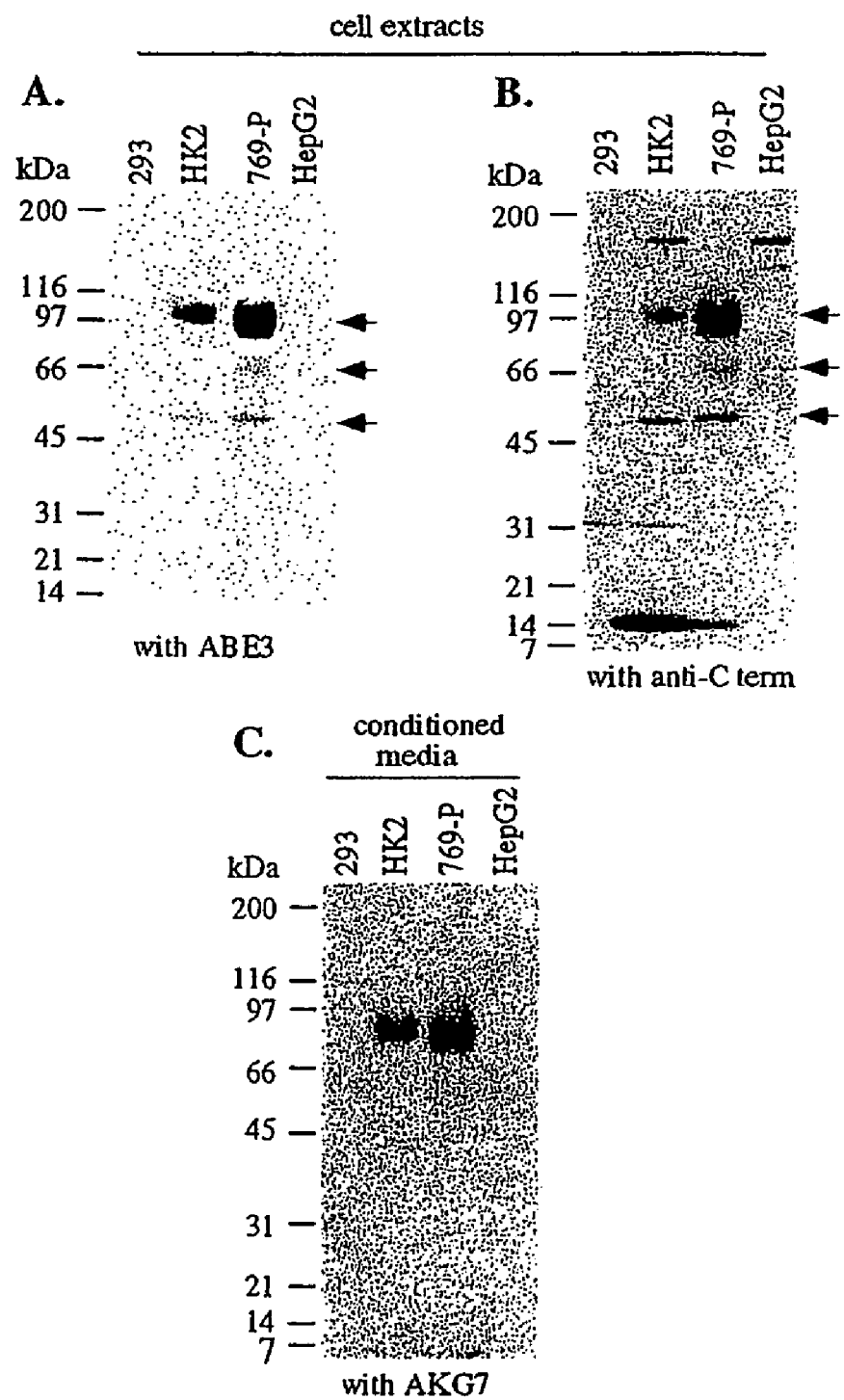

Western blot analysis of the cellular extracts using ABE3 (FIG. 2A) revealed the expression of KIM-1 in the kidney carcinoma cell line (lane 3) as well as in the transformed renal proximal tubule cell line HK2 (lane 2); one major band at about 100 kDa as well as two other bands at about 70 kDa and 50 kDa were detected. This pattern resembled the expression pattern previously observed for the rat KIM-1 protein, which also appeared as three distinct bands after SDS-PAGE (Ichimura et al., J. Biol. Chem. 273:4135–42). The same three bands were also observed with a polyclonal antiserum raised against a synthetic peptide corresponding to the C-terminus of human KIM1(b) (FIG. 2B).

Expression of KIM-1 could not be detected in the transformed embryonic kidney cell line 293 or in the hepatocarcinoma cell line HepG2. Although the expected size for the human KIM1 polypeptide is 36 kDa, the protein band is expected to be detected at a much higher apparent molecular weight, as the protein presents four potential sites for N-glycosylation and multiple O-glycosylation sites.

Cell surface biotinylation of 769-P cells revealed that the 100 kDa KIM-1 band was the actual cell surface protein. The other bands most likely corresponded to KIM-1 processing intermediates transiting through the Golgi.

Western blot analysis of the conditioned culture media using AKG7 monoclonal antibody (FIG. 2C) revealed the presence of a soluble KIM-1 protein migrating at about 90 kDa. The 90 kDa band was also detected with ACA12 monoclonal antibody, but not with the ABE3 monoclonal antibody, or anti-KIM1(b) C-terminal antibodies. A protein band at about 14 kDa was also detected with the anti-KIM1(b) C-terminus serum. Although this band could be unrelated to KIM-1, it is also possible that the 14 kDa band represents the C-terminal product of a cell surface cleavage of KIM1(b).

The 10 kDa decrease in size, as well as the loss of ABE3 binding, could be the result of a cell surface proteolytic cleavage releasing a soluble form into the extracellular milieu. Alternatively, the soluble form could arise from an alternative splicing event, in which the protein produced as a result of the alternative splicing lacked the transmembrane and cytoplasmic domains.

Figure 3:
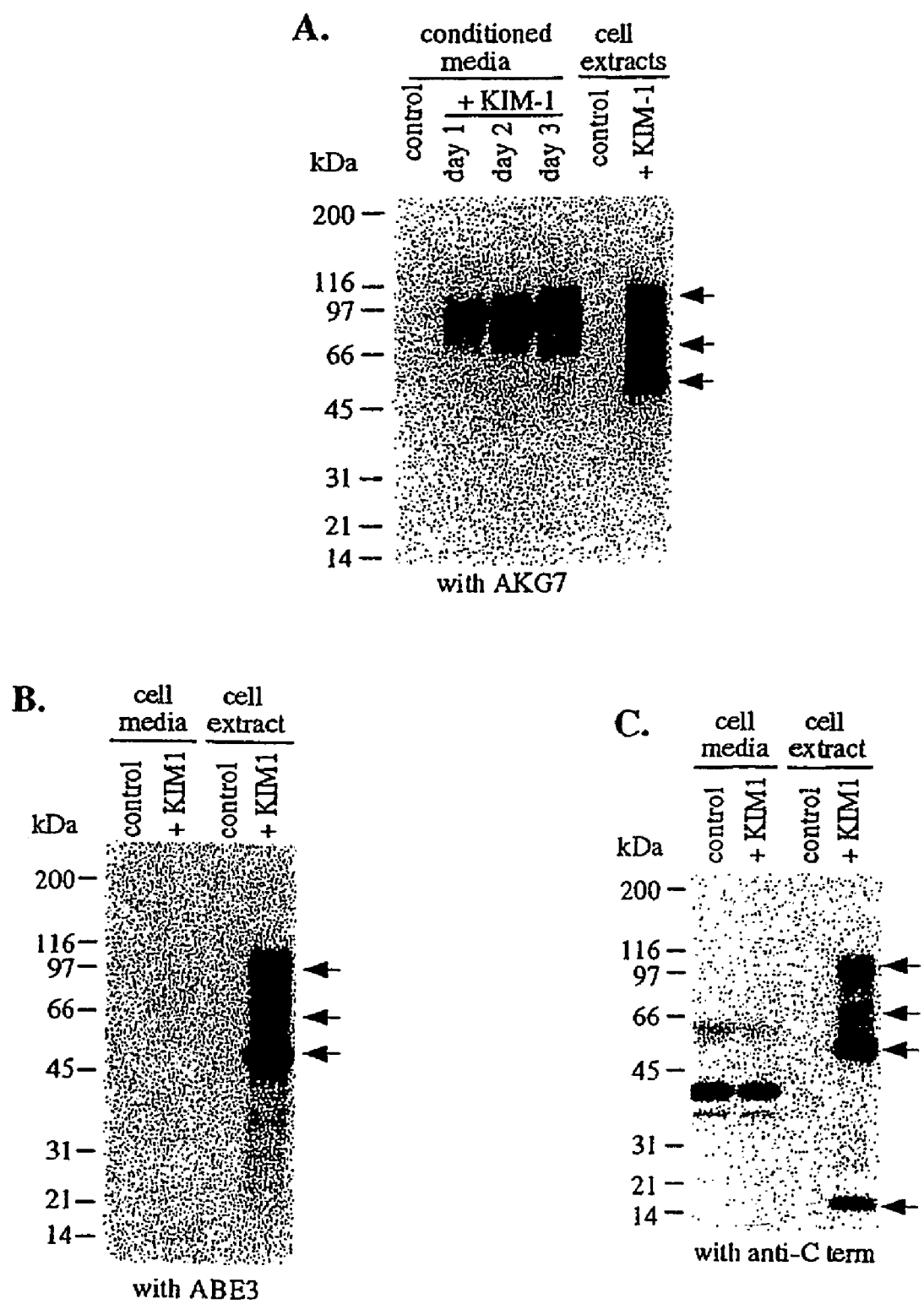

To address the possibility that the 90 kDa soluble human KIM-1 form might arise from alternative splicing of KIM-1 mRNA, recombinant human KIM-1 was expressed from a KIM-1 cDNA construct (FIGS. 3A–3C). KIM-1(b) cDNA was cloned in a vector for constitutive overexpression (pEAG347) in mammalian cells. The resulting plasmid, phKIM1.2, and pEAG347 were used to transfect COS-7 cells. Transformed cells were grown until they reached confluency (about 4 days after transfection). Aliquots of conditioned medium of KIM-1 expressing cells were taken after 1 and 2 days. At day 4, the conditioned media were harvested and the cells were processed as described in the previous section to obtain the cellular extract. The samples were analyzed by western blot with AKG7 (FIG. 3A), ABE3 (FIG. 3B) or polyclonal antibody raised against the carboxy terminus of hKIM1(b) (FIG. 3C).

Analogous to the pattern observed with native human KIM-1 from kidney cell lines, the recombinant KIM-1(b) appeared as several bands corresponding to the various post-translationally modified forms of the protein. Analysis of cell culture supernatant using AKG7 also showed very clearly that a soluble form of KIM-1 was released and accumulated in the cell culture medium. The released recombinant KIM-1, like soluble native KIM-1, was not detected with anti-h KIM1(b) C-terminal antibodies. It was also undetected with ABE3, although a faint band was sometimes observed at high concentration of the protein. This observation suggested that part of the epitope was left after cleavage allowing some weak binding of the antibody. A 14 kDa band was also detected in the cellular extract exclusively with the anti-hKIM-1(b)-C terminal polyclonal antibodies.

Together, these data revealed that soluble KIM-1 was released into the extracellular milieu by proteolytic cleavage at a site proximal to the transmembrane domain, and overlapping with the ABE3 binding epitope. N-terminal sequencing analysis by Edman degradation of the soluble KIM-1 isolated by immunoprecipitation and SDS□PAGE identified the sequence SVKVGGEAGPXVXLX (SEQ ID NO:5) indicating that either the actual signal sequence is four residues longer than the predicted signal sequence determined by the method of von Heijne using the PSORT II program or that the N-terminus is clipped after the removal of the signal peptide.

EXAMPLE 4

Inhibition of Shedding KIM-1 Polypeptide with ABE3 Monoclonal Antibody

Figure 4:
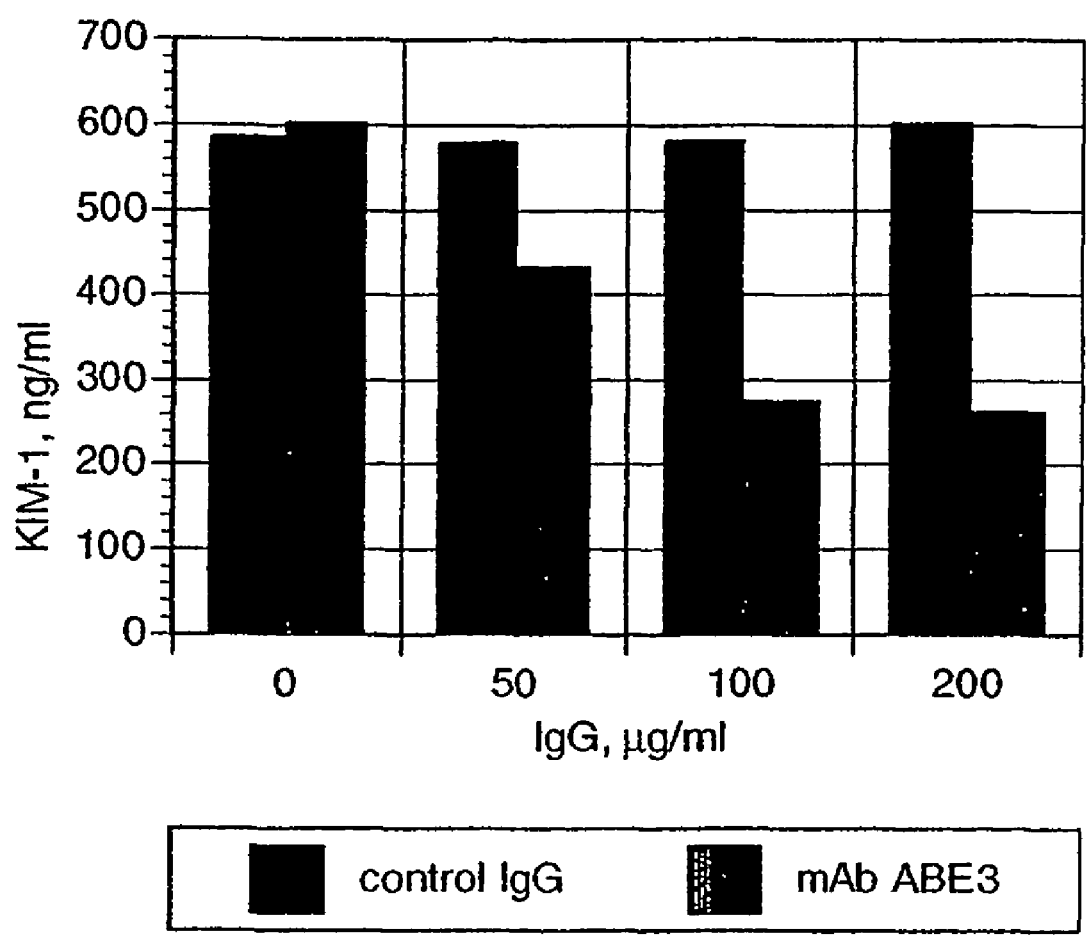
FIG. 4 is a histogram showing the concentration of soluble KIM-1 in conditioned medium of COS-7 cells expressing KIM-1(b) and grown in the presence of different concentrations of ABE3 or a control murine IgG.

To examine the effect of ABE3 monoclonal antibody on proteolytic release of KIM-1, COS-7 cells expressing transiently human KIM-1(b) were grown for 2 days in the presence of various concentrations of ABE3 or mouse IgG as a negative control (FIG. 4).

For transient expression of human recombinant KIM-1 (b), COS-7 cells were transfected by electroporation with 10 μg of plasmid DNA per $10^6$ cells. Transfected cells were plated and grown in DMEM with 4 mM glutamine and 10% fetal bovine serum. After 4 hours of incubation to allow the cells to attach, the medium was replaced with fresh medium. Cell confluency was then approximately 20%. For the shedding inhibition studies, transfected cells were plated in wells of 12-well plates and grown in medium supplemented with various concentrations of ABE3 or mouse IgG (Sigma) as a negative control. Experiments were carried out in triplicates. After 2 days of incubation, the conditioned media were collected from the wells, clarified by centrifugation and assayed by ELISA using purified KIM-1-Ig as a standard.

The results are shown in FIG. 4. While the addition of non-specific mouse IgG did not affect the level of soluble KIM-1 in the medium, there was a significant decrease of soluble KIM-1 when ABE3 was present in the medium. It is thus possible to inhibit partially the proteolytic release of the KIM-1 by competition binding with the ABE3 antibody. This confirmed that the KIM-1 cleavage site lies at, or close to, the binding site of ABE3.

It is conceivable that the release of soluble KIM-1 could result from a high sensitivity of KIM-1 to non-specific proteases at the ABE3 binding site. However, cleavage was not observed of a C-terminus of a recombinant soluble KIM-1 corresponding to the entire extracellular domain with 6 histidine residues at the C-terminus and expressed transiently in the same medium as the full-length KIM-1.

EXAMPLE 5

Inhibition of KIM-1 Polypeptide Shedding with Metalloproteinase Inhibitors

Metalloproteinases (MMPs) or a desintegrin and metalloprotease (ADAMs) have been implicated in the specific cleavage of cell-surface proteins. The effect of two MMP inhibitors on cleavage of KIM-1 polypeptides was examined.

BB-94 (batismatat) and GM6001 (Ilomastat), are two broad spectrum hydroxamic acid-based zinc metalloproteinase inhibitors which inhibit several matrix metalloproteinases (MMP) (20). BB-94 is also a potent inhibitor of TACE (TNF alpha converting enzyme) (18). The activity of these two inhibitors on the shedding of KIM-1 in cell culture was examined.

Figure 5:
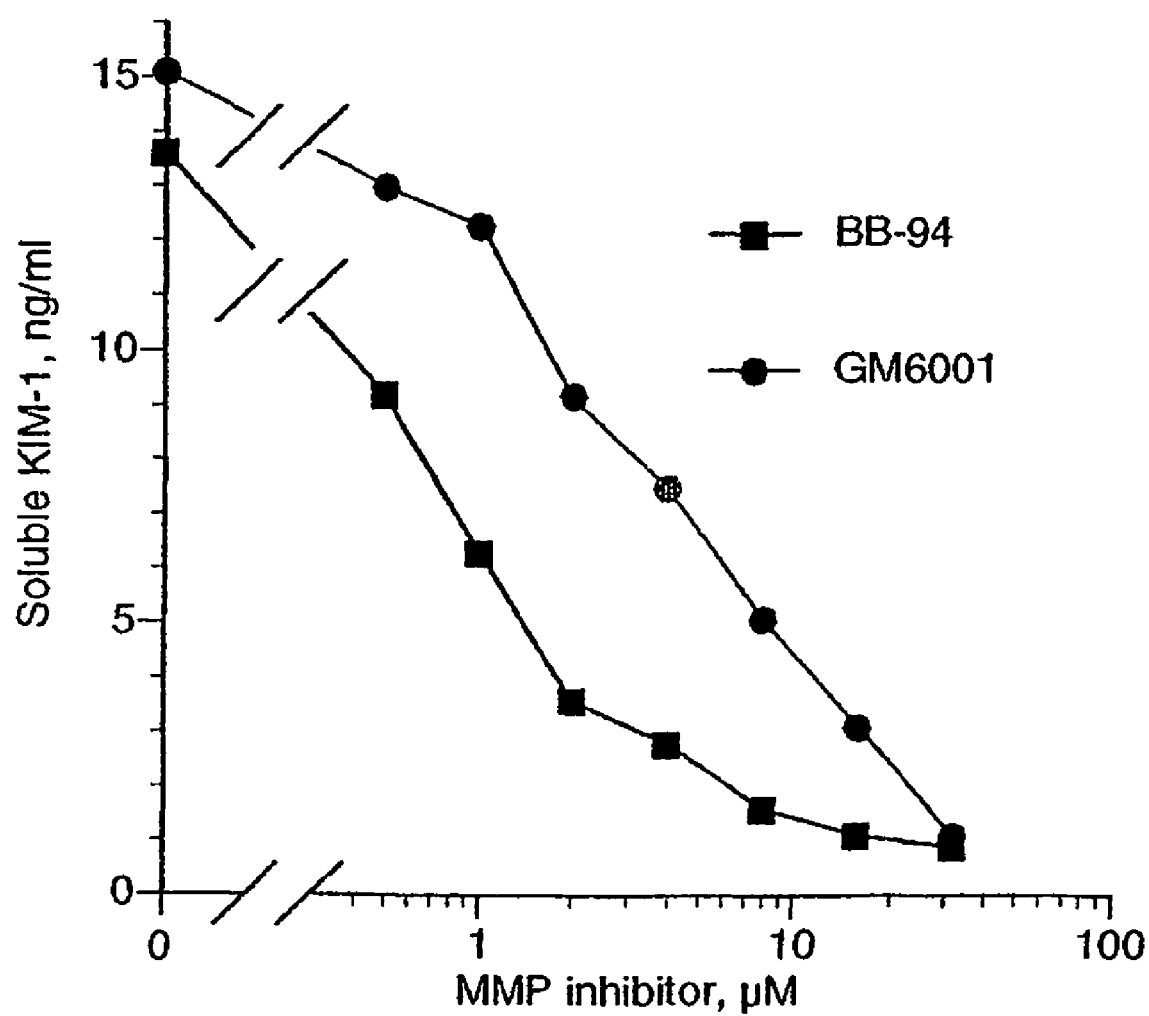
FIG. 5 is a graph showing the concentration of soluble KIM-1 in the conditioned medium of 769-P cells grown in the presence of different concentrations of BB-94 or GM6001 MMP inhibitors.

Stock solutions of BB-94 and GM6001 were maintained in DMS0 at a concentration of 70 mM for BB-94 and 2.5 mM for GM6001. Compounds were diluted directly into fresh medium to concentrations ranging from 0.5 μm to 32 μm. Renal carcinoma cells 769-P were grown in RPMI medium supplemented with 10% fetal bovine serum, 10 mM HEPES, and 1 mM sodium pyruvate, and in the presence of various concentrations of BB-94 and GM6001 for 28 hours. The absence of cytotoxicity of the two compounds was verified by checking cell viability at the end the 28h-culture period using the mitochondria dye MTT (19)(21). The amount of soluble KIM-1 released into the extracellular milieu during the 28h-period was measured by ELISA (FIG. 5).

A complete inhibition of KIM-1 shedding was achieved in the presence of 32 μM of either MMP inhibitors. BB-94 appeared slightly more effective with an $IC_{50}$ of about 1 μM compared to GM 6001 for which the $IC_{50}$ was about 4 μM. These results indicated that the cleavage of KIM-1 is mediated by a metalloproteinase, possibly a member of the MMP or the ADAM families.

Other embodiments are within the following claims.

---

What is claimed is:

1. An isolated monoclonal antibody or antigen-binding-fragment thereof that binds to the extracellular domain of the human KIM-1 polypeptide of SEQ ID NO:7 at an epitope within or overlapping the amino acid sequence: SSDGL-WNNNQTQLFLEHS (SEQ ID NO:1).

2. An isolated antibody or antigen-binding-fragment thereof that has the same epitope specificity as the antibody produced by the hybridoma deposited in the ATCC under Accession No. PTA-3350.

3. An isolated antibody or antigen-binding-fragment thereof that crossblocks binding of the antibody produced by the hybridoma deposited in the ATCC under Accession No. PTA-3350.

4. The isolated antibody or antigen-binding fragment thereof of claim 1, wherein the monoclonal antibody is a humanized antibody.

5. The isolated antibody or antigen-binding-fragment thereof of claim 1, wherein the monoclonal antibody is a fully human antibody.

6. A conjugate comprising the isolated antibody or antigen-binding fragment thereof of claim 1, 2 or 3 linked to a detectable label.

7. A conjugate or fusion polypeptide comprising the isolated antibody or antigen-binding fragment thereof of claim 1, 2 or 3 and a toxin moiety.

8. An antibody produced by the hybridoma deposited with ATCC under Accession No. PTA-3350.

9. Hybridoma ABE3, deposited with ATCC under Accession No. PTA-3350.

10. A composition comprising the isolated antibody or antigen-binding fragment thereof of claim 1, 2 or 3 and a pharmaceutically acceptable carrier.

11. An isolated antibody or antigen-binding fragment thereof that binds to the extracellular domain of the human KIM-1 polypeptide of SEQ ID NO:7 at an epitope within the amino acid sequence: SSDGLWNNNQTQLFLEHS (SEQ ID NO: 1).

12. The isolated antibody or antigen-binding fragment thereof of claim 2, wherein the antibody is a humanized antibody.

13. The isolated antibody or antigen-binding fragment thereof of claim 3, wherein the antibody is a humanized antibody.

14. The isolated antibody or antigen-binding fragment thereof of claim 11, wherein the antibody is a humanized antibody.

15. The isolated antibody or antigen-binding fragment thereof of claim 2, wherein the antibody is a fully human antibody.

16. The isolated antibody or antigen-binding fragment thereof of claim 3, wherein the antibody is a fully human antibody.

17. The isolated antibody or antigen-binding fragment thereof of claim 11, wherein the antibody is a fully human antibody.

18. The isolated antibody or antigen-binding fragment thereof of claim 2, wherein the antibody is a monoclonal antibody.

19. The isolated antibody or antigen-binding fragment thereof of claim 3, wherein the antibody is a monoclonal antibody.

20. The isolated antibody or antigen-binding fragment thereof of claim 11, wherein the antibody is a monoclonal antibody.

21. The isolated antibody or antigen-binding fragment thereof of claim 1, wherein the monoclonal antibody is a single chain antibody.

22. The isolated antibody or antigen-binding fragment thereof of claim 2, wherein the antibody is a single chain antibody.

23. The isolated antibody or antigen-binding fragment thereof of claim 3, wherein the antibody is a single chain antibody.

24. The isolated antibody or antigen-binding fragment thereof of claim 11, wherein the antibody is a single chain antibody.

25. The isolated antibody or antigen-binding fragment thereof of claim 1, wherein the monoclonal antibody or antigen-binding fragment thereof is a chimeric antibody, an $F_{ab}$ fragment, an $F_{(ab')2}$ fragment, an $F_{ab'}$ fragment, an $F_{sc}$ fragment, or an $F_v$ fragment.

26. The isolated antibody or antigen-binding fragment thereof of claim 2, wherein the antibody or antigen-binding fragment thereof is a polyclonal antibody, a chimeric antibody, an $F_{ab}$ fragment, an $F_{(ab')2}$ fragment, an $F_{ab'}$ fragment, an $F_{sc}$ fragment, or an $F_v$ fragment.

27. The isolated antibody or antigen-binding fragment thereof of claim 3, wherein the antibody or antigen-binding fragment thereof is a polyclonal antibody, a chimeric antibody, an $F_{ab}$ fragment, an $F_{(ab')2}$ fragment, an $F_{ab'}$ fragment, an $F_{sc}$ fragment, or an $F_v$ fragment.

28. The isolated antibody or antigen-binding fragment thereof of claim 11, wherein the antibody or antigen-binding fragment thereof is a polyclonal antibody, a chimeric antibody, an $F_{ab}$ fragment, an $F_{(ab')2}$ fragment, an $F_{ab'}$ fragment, an $F_{sc}$ fragment, or an $F_v$ fragment.

29. An isolated antibody or antigen-binding-fragment thereof that binds to the extracellular domain of the human KIM-1 polypeptide of SEQ ID NO:7, when expressed on the surface of a cell, at an epitope within or overlapping the amino acid sequence: SSDGLWNNNQTQLFLEHS (SEQ ID NO:1).

30. The isolated antibody or antigen-binding fragment thereof of claim 29, wherein the antibody is a humanized antibody.

31. The isolated antibody or antigen-binding fragment thereof of claim 29, wherein the antibody is a fully human antibody.

32. The isolated antibody or antigen-binding fragment thereof of claim 29, wherein the antibody is a monoclonal antibody.

33. The isolated antibody or antigen-binding fragment thereof of claim 29, wherein the antibody is a single chain antibody.

34. The isolated antibody or antigen-binding fragment thereof of claim 29, wherein the antibody or antigen-binding fragment thereof is a polyclonal antibody, a chimeric antibody, an $F_{ab}$ fragment, an $F_{(ab')2}$ fragment, an $F_{ab'}$ fragment, an $F_{sc}$ fragment, or an $F_v$ fragment.

35. The isolated antibody or antigen-binding fragment thereof of claim 29, wherein the antibody or antigen-binding fragment thereof binds to an epitope within the amino acid sequence: SSDGLWNNNQTQLFLEHS (SEQ ID NO: 1).

36. The isolated antibody or antigen-binding fragment thereof of claim 29, wherein the antibody is a humanized antibody.

37. The isolated antibody or antigen-binding fragment thereof of claim 35, wherein the antibody is a fully human antibody.

38. The isolated antibody or antigen-binding fragment thereof of claim 35, wherein the antibody is a monoclonal antibody.

39. The isolated antibody or antigen-binding fragment thereof of claim 35, wherein the antibody is a single chain antibody.

40. The isolated antibody or antigen-binding fragment thereof of claim 35, wherein the antibody or antigen-binding fragment thereof is a polyclonal antibody, a chimeric antibody, an $F_{ab}$ fragment, an $F_{(ab')2}$ fragment, an $F_{ab'}$ fragment, an $F_{sc}$ fragment, or an $F_v$ fragment.

* * * * *